US008114413B2

(12) United States Patent (10) Patent No.: US 8,114,413 B2
Majmudar (45) Date of Patent: Feb. 14, 2012

(54) COMPOSITIONS OF MARINE BOTANICALS TO PROVIDE NUTRITION TO AGING AND ENVIRONMENTALLY DAMAGED SKIN

(75) Inventor: Gopa Majmudar, Irving, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 12/817,870

(22) Filed: Jun. 17, 2010

(65) Prior Publication Data

US 2010/0255025 A1    Oct. 7, 2010

Related U.S. Application Data

(63) Continuation of application No. 11/937,960, filed on Nov. 9, 2007, now Pat. No. 7,758,864, which is a continuation of application No. 11/300,641, filed on Dec. 14, 2005, now Pat. No. 7,303,753, which is a continuation of application No. 10/751,684, filed on Jan. 5, 2004, now Pat. No. 7,025,966.

(60) Provisional application No. 60/527,568, filed on Dec. 5, 2003.

(51) Int. Cl.
*A61K 36/02* (2006.01)
*A61K 31/74* (2006.01)
(52) U.S. Cl. ................... 424/195.17; 424/78.03
(58) Field of Classification Search ............... None
See application file for complete search history.

(56) References Cited

U.S. PATENT DOCUMENTS

| | | | |
|---|---|---|---|
| 4,758,283 A | 7/1988 | Takemura et al. | 127/36 |
| 5,153,230 A | 10/1992 | Jaffery | 514/458 |
| 5,378,461 A | 1/1995 | Neigut | 424/94.1 |
| 5,508,033 A | 4/1996 | Briand | 424/195.17 |
| 5,720,963 A | 2/1998 | Smith | 424/401 |
| 5,801,192 A * | 9/1998 | Dumas et al. | |
| 6,086,886 A | 7/2000 | Guo | 424/195.17 |
| 6,495,126 B1 | 12/2002 | Schlitz | 424/78.02 |
| 6,524,599 B2 | 2/2003 | Pinnell | 424/401 |
| 2002/0192245 A1 | 12/2002 | Jensen et al. | 424/401 |
| 2003/0215471 A1 * | 11/2003 | Wilmott et al. | |
| 2005/0036963 A1 | 2/2005 | Sah et al. | 424/62 |

FOREIGN PATENT DOCUMENTS

| | | |
|---|---|---|
| FR | 2657011 | 7/1991 |
| FR | 2703907 | 10/1994 |
| JP | 01093508 | 4/1989 |
| JP | 9-67266 | 3/1997 |
| JP | 11-335293 | 12/1999 |
| JP | 2000072642 | 3/2000 |
| KR | 2001/000373 | 1/2001 |
| UA | 71548 C2 | 12/2004 |
| WO | WO 91/07946 | 6/1991 |
| WO | WO 01/21153 | 3/2001 |
| WO | WO 2005/055736 | 6/2005 |

OTHER PUBLICATIONS

"A Moisturizing Makeover," About H2O Plus, Press Archive, Posted on Sep. 1, 2001.

"Achieve Balance In and Out," About H2O Plus, Press Archive, Posted on Oct. 21, 2002.
"Beauty Flash Balm," Product Information printed from us.clarins. com, printed May 22, 2008.
"H20 Plus Hydrating Body Butter," Product Information printed from Amazon.com, printed May 22, 2008.
"H2O Plus Night Oasis® Oxygenating Rejuvenator," Product Information printed from Amazon.com, printed May 22, 2008.
"Magnify Your Moisture," About H2O Plus, Press Archive, Posted on Oct. 24, 2003.
"Plump Up Your Pucker," About H2O Plus, Press Archive, Posted on Oct. 2, 2002.
"Replenish and Nourish While You Sleep," About H2O Plus, Press Archive, Posted on Jul. 29, 2003.
"Stabilize Your Skin," About H2O Plus, Press Archive, Posted on Oct. 5, 2002.
AltMedDex® System. Thomson Micromedex, Greenwood Village, Colorado, Jun. 2001.
Awad, "Biologically active steroid from the green Ulva lactuca," *Phytotherapy Research*, 14:6414-643, 2000.
Barany and Merrifield, In: *The Peptides, Gross and Meienhofer* (Eds.), Academic Press, NY, 1-284, 1979.
Blumenthal et al., In: *Herbal Medicine, Expanded Commission E Monographs*, 1st Ed., Integrated Medicine Communications, Newton, MA, 2000.
Cornline-Consumer Goods, Beauty & Health Foods: "Iki-Iki Kaoku," by Chlorella Industry, 1997.
Farag et al., "The essential oils of foriander, common dill and bitter fennel and their effects on diabetic rats," Univ. of Cairo, *Bull. Fac. Agric.*, 43(1):31-44, 1992.
Houghten, "General method for the rapid solid-phase synthesis of large numbers of peptides: specificity of antigen-antibody interaction at the level of individual amino acids," *Proc. Natl. Acad. Sci., USA*, 82(15):5131,5135, 1985.
http://nomen.at/Crithmum%20maritimum, Monmen.at-animals and plants, "27 definitions of Crithmum maritimum," downloaded on Jul. 20, 2009.
http://tess2.usto.gov/gin/showfield?f-doc&state+rh4tod.2.1, Trademark electronic search system (TESS) result on "Collastine-Registered Trademark," 2005. http://www.cellex-c.com/pro_side/ssofm/ssofm_txt.html. Cellex-C enhancers. Sea Silk Oil-Free Moisturizer, Sep. 11, 2001.
http://www.pab.fr/acollas.htm., Collastine-registered trademark: anti-wrinkle firmness skin care with marine extract, 2005.
International Product Alert, La Prairie Cellular Body Emulsion, vol. 19, 2002.
International Product Alert, La Prairie Cellular Buffing Oil Manufacturer: La Prairie Category: 311-Skin Care., vol. 19, 2002.
Jacinthe et al., "Microbial nitrogen cycling processes in a sulfidic coastal marsh," *Wetlands Ecology and Management*, 14:123-131, 2006.
Merrifield, "Solid phase synthesis," *Science*, 232(4748)341-347, 1986.

(Continued)

*Primary Examiner* — Michele Flood
(74) *Attorney, Agent, or Firm* — Fulbright & Jaworski L.L.P.

(57) ABSTRACT

The present invention relates to methods and compositions comprising marine botanicals for treating aged, mature, nutritionally-compromised, or environmentally-damaged skin. These methods and compositions provide improvements in the skin's visual appearance, physiological functions, clinical properties, and biophysical properties.

6 Claims, No Drawings

OTHER PUBLICATIONS

Modified Substantive Examination Adverse Report, issued in Malaysian Patent Application No. PI 20045018, dated Aug. 3, 2007.
Non-Final Office action, issued in U.S. Appl. No. 10/751,684, dated Dec. 16, 2004.
Non-Final Office action, issued in U.S. Appl. No. 10/751,684, dated Apr. 7, 2005.
Non-Final Office action, issued in U.S. Appl. No. 11/300,641, dated Jan. 19, 2007.
Non-Final Office action, issued in U.S. Appl. No. 11/300,641, dated May 4, 2007.
Non-Final Office action, issued in U.S. Appl. No. 11/937,960, dated Dec. 17, 2008.
Non-Final Office action, issued in U.S. Appl. No. 11/937,960, dated Apr. 15, 2009.
Non-Final Office action, issued in U.S. Appl. No. 11/937,960, dated Aug. 7, 2009.
Office Action, issued in Eurasian Patent Application No. 200601107128, dated Feb. 15, 2008.
Official Action, issued in Ukrainian Patent Application No. 2006 07458/M, dated Apr. 30, 2008 (English Translation).
Official Action, issued in Ukrainian Patent Application No. 2006 07458, dated Feb. 13, 2008 (English Translation).
Packman-Gans, "Topical moisturizers: quantification of their effect on superficial facial lines," *J. Soc. Cosmetic Chem.*, 29:79-98, 1978.
PCT International Preliminary Report on Patentability, issued in International Patent Application No. PCT/US2004/040332, dated Sep. 18, 2007.
PCT International Preliminary Report on Patentability, issued in International Patent Application No. PCT/US2004/040332, dated Aug. 2, 2007.
PCT International Search Report and Written Opinion, issued in International Application No. PCT/US04/40332, dated Aug. 16, 2007.
PCT International Search Report, issued in International Application No. PCT/US04/040332, dated Jun. 11, 2007.
Product Alert, Blue Anti-Aging Day Crème SPF 12: Retinol & Vitamin C Treatment Crème Manufacturer, Skin Blue Category: 311-Skin Care, vol. 32, 2003.
Remington's Pharmaceutical Sciences, 18$^{th}$ Ed. Mack Printing Company, 1990.
Ruberto et al., "Antioxidant and antimicrobial activity of *Foeniculum vulgare* and *Crithmum maritimum* essential oils," *Planta Med.*, 66:687-693, 2000.
Ruperez et al., "Potential antioxidant capacity of sulfated polysaccharides from the edible marine brown seaweed *Fucus vesiculosus*," *J. Agric. Food Chem.*, 50(4):840-845, 2002.
Schlitz et al., "Retinoic acid induces cyclic changes in epidermal thickness and dermal collagen and glycosaminoglycan biosynthesis rates," *J. Investigative Dermatology*, 87:663-667, 1986.
Singh et al., "Inhibitory potential of chlorella vulgaris (E-2S) on mouse skin papillomagenesis and xenobiotic detoxification system," *Anticancer Research*, 19:1887-1892, 1999.
Stewart and Young, In: Solid Phase Peptide Synthesis, 23-64, Freeman, San Francisco, 1969.
Supplemental Search Report, issued in Eurasian Patent Application No. 200601107128, dated Nov. 3, 2007.
Tam et al., "$S_N2$ deprotection of synthetic peptides with a low concentration of HF in dimethyl sulfide: evidence and application in peptide synthesis," *J. Am. Chem. Soc.*, 105:6442, 1983.
Taiwanese Office Action with search report, issued in Taiwanese Patent Application No. 093137535, dated Sep. 17, 2010 (English translation of search report).

* cited by examiner

COMPOSITIONS OF MARINE BOTANICALS TO PROVIDE NUTRITION TO AGING AND ENVIRONMENTALLY DAMAGED SKIN

CROSS-REFERENCES TO RELATED APPLICATIONS

This application is a continuation of U.S. application Ser. No. 11/937,960, filed Nov. 9, 2007, which is a continuation of U.S. application Ser. No. 11/300,641, filed Dec. 14, 2005 (now issued as U.S. Pat. No. 7,303,753), which is a continuation of U.S. application Ser. No. 10/751,684, filed Jan. 5, 2004 (now issued as U.S. Pat. No. 7,025,966), which claims the benefit of U.S. Provisional Patent Application No. 60/527,568, filed Dec. 5, 2003. The contents of these applications are incorporated by reference.

BACKGROUND OF THE INVENTION

A. Field of the Invention

The present invention relates generally to treatment methods and compositions for improving the skin's visual appearance. In particular, the present invention is directed towards compositions and methods for their use comprising a combination of marine botanicals that can improve the skin's visual appearance by providing improvements in, for example, skin moisture, dryness, surface fine lines, wrinkles, firmness, and/or softness.

B. Background of the Invention

With chronological age, chronic exposure to adverse environmental factors, or malnutrition, the visual appearance, physical properties, and physiological functions of skin change in ways that are considered cosmetically undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Several different approaches can be used to treat damaged skin caused by aging, environmental factors, chemicals, or malnutrition. One approach involves the use of specific agents to directly stimulate or inhibit selected biochemical targets. Examples include the use of retinoids to stimulate collagen and glycosaminoglycan synthesis by fibroblasts (Schiltz, et al., 1986). Another approach is to use agents or processes that stimulate the rate at which the epidermis replaces itself, a process known as epidermal cell renewal. Increases in epidermal cell renewal rates usually result from a more rapid rate of replication of epidermal basal cells, and can be caused by diverse stimuli such as chemical or physical injury, adverse environmental conditions, or direct stimulators of basal cell division.

Some examples of chemical injury include allergic or non-allergic contact irritation, pH extremes, or interaction of the stratum corneum with household or industrial chemicals or pollutants. Physical injury can include skin abrasion, friction (i.e. on the soles and heels of the feet), or removal of the stratum corneum by physical exfoliation (i.e. cosmetic masks) or by tape stripping. Agents that directly or indirectly stimulate basal cell division include retinoids and barrier disrupters. For example, U.S. Pat. No. 5,720,963 discloses that a combination of hydroxy acids, retinoids, and cerebrosides causes chronic injury to the stratum corneum and results in epidermal and dermal repair of the structurally-deteriorated skin. U.S. Pat. No. 6,495,126, for example, uses a combination of surfactants and chelating agents to stimulate an endogenous stratum corneum chymotryptic proteinase that causes a loosening of corneocytes, resulting in an increased rate of epidermal replacement and chronic anti-aging benefits. Adverse environmental exposures that can result in more rapid epidermal turnover rates include UVA, UVB, and IR radiation from the sun and cold coupled with low relative humidity (i.e. low dew point).

Several methods of increasing stratum corneum renewal rates have various drawbacks, such as significant irritation to the skin, skin toxicity, or low pH. In addition, most of these methods involve the invocation of chronic damage to the skin, which sets up repair mechanisms. For most of the existing treatments, there will be a period of time, up to several weeks or months, during which the skin becomes irritated and after which tolerance sets in and the symptoms of irritation may decrease and/or cease.

SUMMARY OF THE INVENTION

The present invention overcomes the deficiencies in the art by providing compositions and methods for their use that can be used to treat aged, mature, nutritionally-compromised, or environmentally-damaged skin.

In one aspect of this invention, the composition comprises at least one, two, or three of the following: algae extract, sea fennel, or *Codium Tomentosum* extract. The composition can be formulated as a cosmetic compound. The composition can also be comprised in a cosmetic vehicle. The cosmetic vehicle can include an emulsion, a cream, a lotion, a solution, an anhydrous base, a gel, or an ointment. The emulsion can be an oil-in-water emulsion or a water-in-oil emulsion. The solution can be an aqueous solution or hydro-alcoholic solution. The anhydrous base can be a lipstick or a powder. The composition can be comprised in an anti-aging product or a moisturizing product. The composition can also be adapted for application at least once, twice, three, four, five, or more times a day during use. In another aspect, the composition can be chemically compatible.

The algae extract can be further defined as a green flower algae extract. The green flower algae extract can be obtained from *Monostroma*. The *Monostroma* that can be used with the present invention can include, for example, *Monostroma nitidium, Monostroma zostericola, Monostroma angicava, Monostroma latissimum, Monostroma bulbosum, Monostroma arcticum, Monostroma areolatum, Monostroma fractum, Monostroma fuscum, Monostroma grevillei, Monostroma leptodermum, Monostroma quaternarium, Monostroma zostericola, Monostroma oxysperum,* or *Monostroma pulchrum*. In another embodiment, the algae extract can be obtained from *Chlorella*. The *Chlorella* can be selected from the group consisting of *Chlorella pyrenoidosa, Chlorella regularis,* and *Chlorella vulgaris*. In particular embodiments, the *Chlorella* is comprised in a composition comprising CHLORELLINE®. In still another embodiment of this invention, the algae extract can be obtained from *Ulva Lactuca*. The *Ulva Lactuca* can be comprised in a composition comprising AOSAINE®. The algae extract can also include *Monostroma, Chlorella,* and *Ulva Lactuca*. In another embodiment, the sea fennel can be comprised in a composition comprising OLEAPHYCOL®. The *Codium Tomentosum* extract can be comprised in a composition comprising CODIAVELANE®.

In a particular aspect of this invention, the composition includes from about 0.001% to about 5.0% of algae extract, from about 0.001% to about 5.0% of sea fennel, and/or from about 0.001% to about 5.0% of *Codium Tomentosum* extract.

Another embodiment of the present invention includes a method of treating or preventing aged or damaged skin comprising topical application of a composition comprising at least one, two, and/or three of the following: algae extract, sea fennel, and *Codium Tomentosum* extract, wherein the application of the composition treats or prevents aged or damaged skin. The composition can be chemically compatible. The composition can also be topically applied in amount effective to increase the stratum corneum turnover rate of the skin. The damaged skin can include nutritionally compromised skin or environmentally damaged skin. The environmentally damaged skin comprises skin damaged by UV light, chronic sun exposure, environmental pollutants, chemicals, disease pathologies, or smoking. The composition can be further defined as a cosmetic composition. The composition can be comprised in a cosmetic vehicle. Other aspects of the composition include those described throughout this specification.

A particular aspect of the present invention includes a composition comprising *Monostroma*, sea fennel, *Codium Tomentosum*, *Chlorella*, and *Ulva Lactuca*, wherein the composition is formulated as a cosmetic compound. The sea fennel can be comprised in a composition comprising OLEAPHYCOL®; the *Codium Tomentosum* can be comprised in a composition comprising CODIAVELANE®; the *Chlorella* can be comprised in a composition comprising CHLORELLINE®; and/or the *Ulva Lactuca* can be comprised in a composition comprising AOSAINE®.

Another embodiment of the invention includes a method of treating or preventing aged or damaged skin comprising topical application of a composition comprising *Monostroma*, sea fennel, *Codium Tomentosum*, *Chlorella*, and *Ulva Lactuca*, wherein the application of the composition treats or prevents aged or damaged skin. The sea fennel can be comprised in a composition comprising OLEAPHYCOL®; the *Codium Tomentosum* can be comprised in a composition comprising CODIAVELANE®; the *Chlorella* can be comprised in a composition comprising CHLORELLINE®; and/or the *Ulva Lactuca* can be comprised in a composition comprising AOSAINE®.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the compositions can also exist as undissolved colloidal suspensions.

The terms "inhibiting," "reducing" or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Aged, nutritionally-compromised, and environmentally-damaged skin effect many people in today's society. Fine lines, wrinkles, loss of elasticity, increased sagging, loss of firmness, loss of color eveness, course surface texture, and mottled pigmentation are just some examples of the effects of damaged skin. Previous attempts to treat damaged skin have various drawbacks ranging from skin irritation to skin toxicity. The present invention is an effective alternative to the use of retinoid compounds or other materials currently used to treat aged or environmentally-damaged skin.

The present invention discloses novel methods and compositions for treating damaged skin. The methods and compositions disclosed in this specification provide treatments that can improve the skin's visual appearance, physiological functions, clinical properties, and biophysical properties by providing nourishment to the skin. Nourishment can be in the form of vitamins, minerals, moisturizers, and/or amino acids. These and other aspect of the present invention are described in further detail below.

A. Marine Botanicals

Compositions of the present invention can include, for example, at least one or any combination of the following compounds and/or extracts: *Monostroma*, sea fennel, *Codium Tomentosum*, *Chlorella*, and *Ulva Lactuca*. In particular embodiments, the sea fennel is comprised in a composition comprising OLEAPHYCOL®. *Codium Tomentosum* can be comprised in a composition comprising CODIAVELANE®. *Chlorella* can be comprised in a composition comprising CHLORELLINE®. *Ulva Lactuca* can be comprised in a composition comprising AOSAINE®.

1. Monostroma

*Monostroma* is a green flower algae that is known to stimulate the proliferation of fibroblast and increase extracellular matrix protein production. The genus of *Monostroma* has many species, including, for example, *Monostroma nitidium, Monostroma zostericola, Monostroma angicava, Monostroma latissimum, Monostroma bulbosum, Monostroma arcticum, Monostroma areolatum, Monostroma fractum, Monostroma fuscum, Monostroma grevillei, Monostroma leptodermum, Monostroma quaternarium, Monostroma zostericola, Monostroma oxysperum*, and *Monostroma pulchrum*. These and other species of *Monostroma* are contemplated as being useful in the present invention.

*Monostroma* can grow in the wild in temperate regions and is also available for purchase as an extract. An air-dried product of *Monostroma* has, for example, the following composition: 16.9% of moisture; 16.6% of proteins; 1.0% of lipids; 47.5% of carbohydrates; 5.6% of fibers; and 12.4% of ash. The carbohydrates comprise polysaccharides containing approximately 60% of L-rhamnose as well as uronic acid, D-xylose, D-glucose, D-mannose and the like. The major part of the carbohydrates is present in the form of rhamnan sulfate (U.S. Pat. No. 4,758,283).

2. OLEAPHYCOL®

OLEAPHYCOL® provides a soothing feeling to the skin and has antioxidant benefits. It comprises marine essential oil minerals and vitamin C. OLEAPHYCOL® is available for purchase from a variety of sources, including, e.g., Presperse, Inc. (www.presperse.com). All forms of OLEAPHYCOL®, including, e.g., OLEAPHYCOL-CM®, OLEAPHYCOL-FV®, and OLEAPHYCOL-LD®, are contemplated as being useful in the present invention. In particular embodiments, OLEAPHYCOL-CM® is preferred. An active ingredient in OLEAPHYCOL-CM® is crithmum maritimum, otherwise known as sea fennel (*Foeniculum vulgaris*).

Sea fennel contains ingredients that are anti-inflammatory and have a tightening effect on the skin. It can be used to strengthen muscle tone and increase the elasticity of the skin. Three bioactive fractions have been identified from sea fennel: falcarinol (panaxynol), falcarindiol, and hreims (Winsauer-Burkett, 2001).

3. CODIAVELANE®

CODIAVELANE®, including CODIAVELANE-BG®, can be used to maintain water balance of the epidermis and provide moisture to the skin. It can be purchased, for example, at Presperse, Inc. CODIAVELANE® includes propylene glycol, water, and *Codium Tomentosum* extract. Other ingredients include proteins, glucuronic acid, and methyl paraben. CODIAVELANE-BG® includes butylene glycol, water, and *Codium Tomentosum* extract.

*Codium Tomentosum*, otherwise known as Algae extract, normalizes and balances skin's moisture content by adding vital oligo-elements and increasing surface hydration. Algae are chlorophyll-containing organisms that includes over 20,000 different known species. In cosmetics, algae are used as thickening agents, water-binding agents, and antioxidants. Other forms of algae, such as Irish moss and carrageenan, contain proteins, vitamin A, sugar, starch, vitamin B1, iron, sodium, phosphorus, magnesium, copper, and calcium. These are all useful as sources for skin care, either as emollients or antioxidants (Ruperez et al., 2002).

4. CHLORELLINE®

CHLORELLINE® contains vitamins, minerals, and amino acids. It can be sued to provide nutrients to skin, including aged or damaged skin. CHLORELLINE® can be purchased at Rita Corporation (www.ritacorp.com) An active ingredient in CHLORELLINE® is *Chlorella*.

*Chlorella* is a genus of unicellular green algae. Species include *Chlorella pyrenoidosa, Chlorella regularis*, and *Chlorella vulgaris*, all of which are contemplated as being useful in the present invention. It can be grown, harvested, purified, and processed into powders, tablets, and other forms. It has antioxidant properties and provides nutrients to skin, including aged or damaged skin. *Chlorella* contains chlorophyll A, chlorophyll B, vitamins A, B1, B2, B6, B12, C, and E, beta-carotene, potassium, sodium, magnesium, iron, calcium, and 19 amino acids, including all 8 essential amino acids. Other ingredients include biotin, inositol, *Chlorella* Growth Factor (CGF), Chlorellan, Dextran Sulfate, fiber, DNA, RNA, enzymes, inositol, phosphorous, protein, sulfolipids, and folic acid.

5. AOSAINE®

AOSAINE® can be used to protect collagen and elastin from degradation, thereby helping to prevent wrinkles and skin aging. It can be purchased, for example, at Presperse, Inc. AOSAINE® optimizes cellular respiration and stimulates collagen production in the skin. It also increases protein synthesis and cell proliferation. It contains a number of amino acids, including lysine, histidine, arginine, aspartic acid, proline, glycine, serine, glutamic acid, alanine, threonine, tyrosine, isoleucine, leucine, and phenyl-alanine. AOSAINE® is a hydrolysate of seaweed proteins of the algae *Ulva Lactuca*.

*Ulva lactuca* extract has a strong permeability which absorbs into the skin quickly, improving blood circulation, increasing metabolism, and discharging subcutaneous fat. It also inhibits elastase activity, which protects protein fibers, collagen and elastase. *Ulva lactuca* can promote skin vitality and cellular proliferation, thereby preserving the epidermis from aging. In addition, *Ulva lactuca* contributes to the production of enzymatic reactions which break down or metabolize fats.

6. Source of Specific Compounds and Extracts

The specific compounds, extracts, and active ingredients in such compounds and extracts contemplated by the present invention can be obtained by any means known to a person of ordinary skill in the art. For example, the compounds, extracts, and active ingredients can be isolated by obtaining the source of such compounds or extracts. The compounds, extracts, or active ingredients can be purified by any number of techniques known to a person of ordinary skill in the art. Such purification techniques include, e.g., Polyacrylamide Gel Electrophoresis, High Performance Liquid Chromatography (HPLC), Gel chromatography or Molecular Sieve Chromatography, and Affinity Chromatography.

In addition, the compounds, extracts, and active ingredients of such compounds and extracts can be obtained by chemical synthesis or by recombinant means by using conventional techniques. For example, various automatic polypeptide synthesizers are commercially available and can be used in accordance with known protocols. See, for example, Stewart and Young, (1984); Tam et al., (1983); Merrifield, (1986); and Barany and Merrifield (1979), Houghten (1985). As for recombinant means, examples include the expression of a nucleic acid sequence encoding a peptide or polypeptide in an in vitro translation system or in a living cell.

7. Equivalents

Known and unknown equivalents to the specific compounds, extracts, and active components in such compounds and extracts discussed throughout this specification can be used with the compositions and methods of the present invention. The equivalents can be used as substitutes for the specific compounds, extracts, and active components. The equivalents can also be used to add to the methods and compositions of the present invention. By way of example, equivalents to *Monostroma*, sea fennel *Codium Tomentosum, Chlorella*, and/or *Ulva Lactuca* can be used with the methods and compositions disclosed in this specification. Related species and genuses to the specific compounds and extracts can also be used with the methods and compounds of the present invention.

A person of ordinary skill in the art would be able to recognize and identify acceptable known and unknown equivalents to the specific compounds, extracts, and active components in such compounds and extracts without undue experimentation.

B. Compositions of the Present Invention

1. Concentrations of Marine Botanical Extracts

A person of ordinary skill would recognize that the compositions of the present invention can include any number of combinations of marine botanical extracts, or derivatives therein. It is also contemplated that the concentrations of the marine botanical extracts of the present invention can vary. In certain non-limiting embodiments, the present compositions may comprise in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 99% or more of at least one marine botanical extract, and any range derivable therein. A person of ordinary skill in the art would understand that the concentrations for the botanical extracts in the compositions of the present invention can vary depending on the addition, substitution, and/or subtraction of additional botanical extracts and acceptable substitutes to these extracts.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

2. Cosmetic Vehicles

The present compositions are effective in all types of cosmetic vehicles. Non-limiting examples of suitable cosmetic vehicles include emulsions, creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention.

In preferred embodiments, the cosmetic vehicle is selected from oil-in-water emulsions, hydro-alcoholic solutions, or encapsulated beads in anhydrous systems. With respect to oil-in-water emulsions, such emulsions and their compositions and methods of making are well known in the art. It is important, however, that the concentrations and combinations of the compounds and extracts be selected in such a way that the combinations are chemically compatible and do not form complexes which precipitate from the finished product.

3. Cosmetic Products

The composition of the present invention can also be used in many cosmetic products including, but not limited to, moisturizing cream, skin benefit creams and lotions, gels, ointments, foundation, night cream, lipstick, cleansers, toners, masks, and/or color cosmetic products. The composition is most preferably used in anti-aging products for the face and other body parts, most especially leave-on products.

4. Additional Compounds and Agents that can be Used in Combination with the Present Compositions Compositions of the present invention can include other beneficial agents and compounds such as, for example, acute or chronic moisturizing agents (including, e.g., humectants, occlusive agents, and agents that affect the natural moisturization mechanisms of the skin), anti-oxidants, sunscreens having UVA and/or UVB protection, skin lightening agents (e.g. hydroquinone), emollients, anti-irritants, vitamins, trace metals, anti-microbial agents, botanical extracts, fragrances, and/or dyes and color ingredients.

i Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea officinalis extract, aluminum starch octenylsuccinate, aluminum stearate, apricot (*prunus armeniaca*) kernel oil, arginine, arginine aspartate, arnica montana extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, *cardamon* (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*oenothera biennis*) oil, fatty acids, fructose, gelatin, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium DNA, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

ii Antioxidants

Non-limiting examples of antioxidants that can be used with the compositions of the present invention include acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

iii Compounds Having Ultraviolet Light Absorbing Properties

Non-limiting examples of compounds that have ultraviolet light absorbing properties that can be used with the compounds of the present invention include titanium dioxide, zinc oxide, benzophenone, benzophenone-1, benzophenone-2, benzophenone-3, benzophenone-4 benzophenone-5, benzophenone-6, benzophenone-7, benzophenone-8, benzophenone-9, benzophenone-10, benzophenone-11, benzophenone-12, benzyl salicylate, butyl PABA, cinnamate esters, cinoxate, DEA-methoxycinnamate, diisopropyl methyl cinnamate, ethyl dihydroxypropyl PABA, ethyl diisopropylcinnamate, ethyl methoxycinnamate, ethyl PABA, ethyl urocanate, glyceryl octanoate dimethoxycinnamate, glyceryl PABA, glycol salicylate, homosalate, isoamyl p-methoxycinnamate, PABA, PABA esters, Parsol 1789, and isopropylbenzyl salicylate.

iv Additional Compounds and Agents

Non-limiting examples of additional compounds and agents that can be used with the compositions of the present invention include skin lightening agents (e.g. kojic acid, hydroquinone, ascorbic acid and derivatives, retinoids and their derivatives, and niacinamide), emollients (e.g. esters and fatty acids), vitamins (e.g. D, E, A, K, and C), trace metals (e.g. zinc, calcium and selenium), anti-irritants (e.g. steroids and non-steroidal anti-inflammatories), antimicrobial agents (e.g. triclosan), botanical extracts (e.g. aloe vera, chamomile, cucumber extract, ginkgo bibloba, ginseng, and rosemary), dyes and color ingredients (e.g. D&C blue no. 4, D&C green no. 5, D&C orange no. 4, D&C red no. 17, D&C red no. 33, D&C violet no. 2, D&C yellow no. 10, D&C yellow no. 11 and DEA-cetyl phosphate), preservatives (e.g. BHA), emollients (i.e. organic esters, fatty acids, lanolin and its derivatives, plant and animal oils and fats, and di- and triglycerides), antimicrobial agents (e.g., triclosan and ethanol), and fragrances (natural and artificial).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Chronic Anti Aging Study

Materials and Methods: The following study was conducted to determine if a marine composition comprising 5.0% CODIAVELANE®, 1.0% AOSAINE®, 2.0% Monostroma, 5.0% OLEAPHYCOL-CM®, and 3.0% CHLORELLINE® (a non-limiting example of a botanical blend of the present invention) provides long-term visual and measurable anti-aging benefits on the human face. Vehicle A (Table 1) was used as a control. Twenty panelists applied the composition twice a day, morning and evening on their face.

TABLE 1

| Vehicle A* | | |
|---|---|---|
| Phase | Ingredient | % In Formula |
| A | Water | 58.4 |
| A | Glycereth-26 | 5.0 |
| A | Hispagel | 5.0 |
| A | Disodium EDTA | 0.05 |
| A | Carbopol 940, 2% | 15.0 |

TABLE 1-continued

| Vehicle A* | | |
|---|---|---|
| Phase | Ingredient | % In Formula |
| B | Lecinol S-10 | 1.0 |
| C | Cosmowax J | 1.25 |
| C | Finsolve TN | 6.0 |
| C | Dimethicone | 0.5 |
| C | Isostearyl Alcohol | 1.25 |
| C | Cetyl Alcohol | 0.7 |
| C | Silica | 0.35 |
| D | Triethanolamine, 99% | 1.16 |
| D | Water | 1.60 |
| E | Germaben II | 1.0 |
| F | Sodium PCA | 0.11 |
| F | Prodew 400 | 0.7 |
| F | Tocopheryl Acetate | 0.1 |
| F | Phospholipid EFA | 0.82 |

*Procedure to make Vehicle A: Add the ingredients in A to vessel, in order, at room temperature, mixing between additions. Begin heating to 75° C. At 50° C., add B. At 75° C. add C, in order, mixing between additions. As mixture cools, add D at 65° C. At 45° C., add E and F.

The panelists were monitored for skin condition at the beginning of the study (i.e. before treatment); at four weeks after the treatment; and at eight weeks after the treatment. They were evaluated for face and neck moisture, dryness, surface fine lines, canthus wrinkles, firmness, softness, and clarity. The results identified in Table 2 were obtained by using the following procedures. Face and neck moisture were evaluated using impedance measurements, an electrical conductivity measurement using the Nova Dermal Phase Meter. Dryness, surface fine lines, and softness were determined by an expert grader using a calibrated visual analog scale from 1 to 10. Skin softness was measured by Gas Bearing Electrodynamometer. Surface fine lines were counted and the severity of the lines evaluated according to the Packman-Gans method, (1978), using weighted scoring. Dryness was evaluated using a calibrated visual analog scale from 1 to 10. Firmness was evaluated using a Hargens ballistometer, a device that evaluates the elasticity and firmness of the skin by dropping a small body onto the skin and recording its first two rebound peaks. As firmness decreases, the second peak will be smaller in comparison to the first. Clarity was evaluated using a Minolta Chromameter, which measures the total light reflected from the skin compared to the amount of red and brown/yellow light. These measurements were mathematically analyzed to determine the clarity of the skin. Canthus wrinkles were evaluated four and eight weeks after treatment by comparing the silicone replicas (negative impressions) made of the individuals' skin at baseline. The replicas were evaluated by computer image analysis to determine the number and depth of the wrinkles.

Results: As shown in Tables 2 and 3, continued improvement was seen for the skin condition parameters throughout the 8 weeks of the study. The composition comprising the marine botanicals performed better than the vehicle A control. A continued improvement was also seen with vehicle A. This was due to the moisturizing ingredients in the vehicle A formula.

TABLE 2

Effects of marine botanical composition on the human skin

| | % Improvement Compared to Baseline | | | |
|---|---|---|---|---|
| | Vehicle A | | Vehicle A + Botanical Blend | |
| Skin Benefit | Week 4 | Week 8 | Week 4 | Week 8 |
| Cheek Moisture | 20.6 | 33.5 | 33.6 | 48.0 |
| Neck Moisture | 27.9 | 36.5 | 35.3 | 49.9 |
| Firmness | 12.1 | 24.4 | 17.0 | 29.0 |
| Softness/Suppleness | 22.2 | 32.4 | 26.0 | 41.1 |
| Canthus Wrinkles | 17.2 | 28.4 | 24.0 | 43.3 |
| Clarity | 4.8 | 8.5 | 5.8 | 11.3 |
| Surface Fine Lines | 18.1 | 29.2 | 23.1 | 41.2 |
| Dryness | 32.7 | 51.0 | 36.4 | 58.6 |

TABLE 3

Panelist self assessment of the marine botanical composition during an 8-Week Treatment Period

| Skin Benefit | % of Panelists Perceiving Much Greater Improved Skin Condition* | | | | | |
|---|---|---|---|---|---|---|
| | Vehicle A | | | Marine botanicals in Vehicle A | | |
| Skin Condition | 2 Weeks | 4 Weeks | 8 Weeks | 2 Weeks | 4 Weeks | 8 Weeks |
| Dryness | 53.3 | 66.7 | 86.7 | 60.00 | 80.00 | 100.0 |
| Smoothness | 46.7 | 60.0 | 80.0 | 60.0 | 73.3 | 100.0 |
| Lines and Wrinkles | 6.7 | 26.7 | 60.0 | 20.00 | 46.7 | 66.7 |
| Firmness | 6.7 | 46.7 | 66.7 | 20.00 | 60.0 | 80.0 |
| Softness | 33.3 | 46.7 | 73.3 | 53.3 | 60.0 | 86.7 |
| Healthy Glow | 13.3 | 26.7 | 46.7 | 26.7 | 33.3 | 66.7 |
| Elasticity | 26.7 | 53.3 | 66.7 | 20.00 | 66.7 | 86.7 |
| Looks Younger | 13.3 | 46.7 | 73.3 | 20.0 | 60.0 | 86.7 |
| Looks Healthier | 20.0 | 46.7 | 80.00 | 26.7 | 60.00 | 86.7 |

*Fifteen panelists in each of the treatment cells participated in the study. After 2, 4, and 8 weeks of product use, the panelists rated their skin condition on a 5-point scale which compared the condition at the start of the study. The scale ranged from the assessed parameter being much less improved, somewhat less improved, no change, somewhat greater improved, and much greater improved. The values represent the percent of panelists who perceived much greater improvement at the given point in time. A person of ordinary skill in the cosmetic arts understands the meaning of the terms used in the far left column of Table 3.

Example 2

Stratum Corneum Turnover Study

Materials and Methods: The following procedure was utilized to estimate stratum corneum turnover rates on human skin, which results directly from epidermal activation. Four sites were marked on the forearm using a plastic template. Baseline readings of color intensity were determined using a Minolta Chromameter (b* value listed in Table 4). Occlusive Hilltop chambers (2 cm diameter) containing 0.05 ml Mary Kay SUN ESSENTIALS® Sunless Tanning Lotion product with dihydroxyacetone (DHA) were placed on the sites. After 6 hours, these patches were removed, and 18 hours later, the color intensity was again determined using the Chromameter. The Δ b* values in Table 4 were calculated as the difference between the reading and the baseline. Panelists applied the formula in Table 5 to the brown spots in the morning and evening during the ensuing 10 days. Chromameter readings were repeated after 4, 7, and, 10 days. The color decay slope was calculated as the percent loss per day, and the transit time determined by extrapolating to 100% loss of color.

Results: The results of this study (Table 4) indicate that the combination of Sea Fennel, Monostroma, and CHLORELLINE® increased the rate at which the stratum corneum replaced itself when compared to the vehicle B (Table 5) that was used to incorporate these three ingredients. The effects were concentration-dependent. The increases in stratum corneum replacement rate show that Sea Fennel, Monostroma, and CHLORELLINE® in the composition activate and/or stimulate the epidermis of the skin.

TABLE 4

Effects of Sea Fennel, Monostroma and CHLORELLINE® on Human Stratum Corneum Turnover Rate

| Composition Tested | Stratum Corneum Renewal Rate (Δ b*/Day) | % Change in Stratum Corneum Renewal Rate vs. No Treatment Control |
|---|---|---|
| Untreated | 0.590 | — |
| Vehicle B (Table 5) | 0.632 | 7 |
| Vehicle B + 0.5% Monostroma + 1.0% CHLORELLINE® | 0.660 | 12 |
| Vehicle B + 2.0% Monostroma + 3.0% CHLORELLINE® | 0.691 | 17 |

TABLE 5

Vehicle B*

| Phase | Ingredient | % In Formula |
|---|---|---|
| A | Water | 87.86 |
| A | Disodium EDTA | 0.10 |
| A | Ferulic Acid | 0.01 |

TABLE 5-continued

Vehicle B*

| Phase | Ingredient | % In Formula |
|---|---|---|
| A | Carbopol ETD 2020 | 0.30 |
| B | Butylene Glycol | 5.00 |
| B | Methylparaben | 0.20 |
| C | L-Arginine | 0.50 |
| C | Water | 5.00 |
| D | Triethanolamine, 99% | 0.25 |
| E | DMDM Hydantoin | 0.20 |
| F | Vegetech Night Breeze | 0.01 |
| F | Sea Rocket Extract | 0.01 |
| F | Elias Blend | 0.05 |
| F | Sea Fennel Extract | 0.01 |
| G | Unispheres PACE | 0.50 |

*Procedure to make Vehicle B: Add the ingredients in B to vessel, in order, at room temperature, mixing between additions. Add phase A to B at room temperature. Add C, D, E and F in order, mixing between additions at room temperature. Slowly add G at the end at room temperature.

All of the compositions and/or methods and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,758,283
U.S. Pat. No. 5,720,963
U.S. Pat. No. 6,495,126
Barany and Merrifield, In: *The Peptides*, Gross and Meienhofer (Eds.), Academic Press, NY, 1-284, 1979.
Blumenthal et al., In: *Herbal Medicine, Expanded Commission E Monographs*, 1st Ed., Integrated Medicine Communications, Newton, Mass., 2000.
Fang et al., Univ. of Cairo, *Bull. Fac. Agric*, 43(1):31-44, 1992.
Houghten, *Proc. Natl. Acad. Sci. USA*, 82(15):5131-5135, 1985.
Merrifield, *Science*, 232(4748):341-347, 1986.
Packman-Gans method, *J. Soc. Cosmetic Chem.* 29:70 (1978
Packman-Gans, *J. Soc. Cosmetic Chem.*, 29:70, 1978.
Remington's Pharmaceutical Sciences, 18th Ed. Mack Printing Company, 1990.
Ruperez et al., *J. Agric. Food Chem.*, 50(4):840-845, 2002.
Schiltz et al. *J. Investigative Dermatology*, 87:663-667, 1986.
Stewart and Young, In: *Solid Phase Peptide Synthesis*, 24-66, Freeman, San Francisco, 1969.
Tam et al., *J. Am. Chem. Soc.*, 105:6442, 1983.
Winsauer-Burkett, *Fennel*, Alt MedDex, June 2001.

What is claimed is:

1. A topical skin composition comprising:
   (a) water;
   (b) *Crithmum maritimum* extract;
   (c) *Ulva lactuca* extract;
   (d) *Chlorella vulgaris* extract;
   (e) amino acids; and
   (f) butylene glycol, a phospholipid, glycerin, retinyl palmitate, tocopheryl acetate, and magnesium ascorbyl phosphate,
   wherein the composition is oil-free.

2. The composition of claim 1, wherein the composition is a gel-based composition.

3. The composition of claim 1, wherein the composition is a lotion.

4. A method of moisturizing skin comprising topically applying to skin in need thereof an effective amount of a composition comprising:
   (a) water;
   (b) *Crithmum maritimum* extract;
   (c) *Ulva lactuca* extract;
   (d) *Chlorella vulgaris* extract;
   (e) amino acids; and
   (f) butylene glycol, a phospholipid, glycerin, retinyl palmitate, tocopheryl acetate, and magnesium ascorbyl phosphate,
   wherein the composition is oil-free.

5. The method of claim 4, wherein the composition is a gel-based composition.

6. The method of claim 4, wherein the composition is a lotion.

* * * * *